(12) United States Patent
Esumi et al.

(10) Patent No.: US 9,700,572 B2
(45) Date of Patent: Jul. 11, 2017

(54) ANTI-CANCER AGENT

(71) Applicants: Kracie Pharma, Ltd., Tokyo (JP); NATIONAL CANCER CENTER, Tokyo (JP); National University Corporation University of Toyama, Toyama-shi (JP)

(72) Inventors: Hiroyasu Esumi, Kashiwa (JP); Masafumi Ikeda, Kashiwa (JP); Chika Miyoshi, Kashiwa (JP); Shigetoshi Kadota, Toyama (JP); Toshiki Okubo, Takaoka (JP); Satoshi Yomoda, Takaoka (JP); Takafumi Fuse, Takaoka (JP); Takanori Kawashima, Takaoka (JP); Shigeki Chiba, Takaoka (JP)

(73) Assignees: National Cancer Center, Tokyo (JP); Kracie Pharma, Ltd., Tokyo (JP); National University Corporation University of Toyama, Toyama (JP)

( * ) Notice: Subject to any disclaimer, the term of this patent is extended or adjusted under 35 U.S.C. 154(b) by 0 days.

(21) Appl. No.: 14/494,637

(22) Filed: Sep. 24, 2014

(65) Prior Publication Data
US 2015/0196576 A1 Jul. 16, 2015

Related U.S. Application Data

(63) Continuation of application No. PCT/JP2013/058692, filed on Mar. 26, 2013.

(30) Foreign Application Priority Data

Mar. 26, 2012 (JP) .................................. 2012-069964

(51) Int. Cl.
| | |
|---|---|
| A61K 31/7048 | (2006.01) |
| A61K 31/7034 | (2006.01) |
| A61K 31/341 | (2006.01) |
| A61K 31/365 | (2006.01) |
| A61K 36/28 | (2006.01) |

(52) U.S. Cl.
CPC ........ *A61K 31/7048* (2013.01); *A61K 31/341* (2013.01); *A61K 31/365* (2013.01); *A61K 31/7034* (2013.01); *A61K 36/28* (2013.01)

(58) Field of Classification Search
None
See application file for complete search history.

(56) References Cited

U.S. PATENT DOCUMENTS

| | | | | |
|---|---|---|---|---|
| 2012/0029070 A1* | 2/2012 | Yamamoto | ........... | A61K 9/1623 514/473 |
| 2013/0190394 A1* | 7/2013 | Zhao | ............... | A61K 9/1075 514/473 |
| 2014/0037770 A1 | 2/2014 | Okubo et al. | ................. | 424/764 |

FOREIGN PATENT DOCUMENTS

| | | | | |
|---|---|---|---|---|
| CN | 101036644 | | 9/2007 | ............ A61K 36/28 |
| EP | 2623107 A1 | | 8/2013 | ............ A61K 36/28 |
| KR | 2008 0107794 A | | 12/2008 | ............ A61K 36/28 |
| WO | WO2010/109961 | * | 9/2010 | |
| WO | WO 2010/109961 A1 | | 9/2010 | ............ A61K 36/28 |
| WO | WO 2012/043549 A1 | | 4/2012 | ............ A61K 36/28 |

OTHER PUBLICATIONS

Awale et al., Cancer Research, vol. 66, No. 3, pp. 1751-1757.*
The Library of National Research Institute of Chinese Medicine, Ministry of Health and Welfare, Eds., "New Findings in Pharmacological Study of Arctiin and Arctigenin," New Findings of Chinese Medicine, Oct. 2011.
The Library of National Research Institute of Chinese Medicine, Ministry of Health and Welfare, Eds., "New Findings in Pharmacological Study of Arctiin and Arctigenin," New Findings of Chinese Medicine, Oct. 2011 (English Translation).
Awale, et al., "Identification of arctigenin as an antitumor agent having the ability to eliminate the tolerance of cancer cells to nutrient starvation," Cancer Research., vol. 66, No. 3, pp. 1751-1757 (Feb. 1, 2006).
Boeck, et al., "Second-line chemotherapy with pemetrexed after gemcitabine failure in patients with advanced pancreatic cancer: a multicenter phase II trial," Annals of Oncology, vol. 18, pp. 745-751(Jan. 17, 2007).
Li, et al., "Implications of cancer stem cell theory for cancer chemoprevention by natural dietary compounds," Journal of Nutritional Biochemistry, vol. 22, pp. 799-806, (2011).
Mueller, et al., "Combined Targeted Treatment to Eliminate Tumorigenic Cancer Stem Cells in Human Pancreatic Cancer," Gastroenterology, vol. 137, No. 3, pp. 1102-1113, (Sep. 2009).
Yoo, et al, "Lignans inhibit cell growth via regulation of Wnt/β-catenin signaling," Food and Chemical Toxicology, vol. 48, pp. 2247-2252, (2010).
European Patent Office, Munich Office, Extended European Search Report, pursuant to Rule 62 EPC, Application PCT/JP2013058692, dated Nov. 20, 2015.

* cited by examiner

*Primary Examiner* — Traviss C McIntosh, III
(74) *Attorney, Agent, or Firm* — Sunstein Kann Murphy & Timbers LLP

(57) ABSTRACT

The present invention is intended to provide a novel anti-cancer agent which is effective to a cancer. After administering an agent prepared using burdock fruit extract to a pancreas cancer patient so that a dose of arctigenin was 100 mg or more per day, the tumor reducing effect was observed, and, in addition, lowering of tumor markers was confirmed. The present invention provides an anticancer agent containing arctigenin, wherein a dose of the arctigenin is 100 mg or more per day. In addition, the present invention provides the anticancer agent containing arctigenin and arctiin at a weight ratio of arctigenin/arctiin=0.7 to 1.3.

6 Claims, 7 Drawing Sheets

ANTI-CANCER AGENT

CROSS REFERENCE

This application is a continuation application of PCT Application No. PCT/JP20131058692 filed Mar. 26, 2013, which claims priority to Japanese Application No. 2012-069964 filed Mar. 26, 2002, the contents of which are herein incorporated by reference in their entirety.

FIELD OF THE INVENTION

The present invention relates to an anticancer agent containing arctigenin. More particularly, the present invention relates to an anticancer agent containing arctigenin with the dosage per day thereof being 100 mg or more.

BACKGROUND ART

A pancreas cancer is one of the refractory cancers, and the 5-year survival rate of the whole pancreas cancer patient is estimated to be 2 to 3%. The number of the patients who died from the pancreas cancer has rapidly increased by approximately 2.5 times for the last 20 years, and the statistics showed that 26,791 people died from the pancreas cancer in 2009. The incidence and mortality of the pancreas cancer is almost same number, and the pancreas cancer occupies 6% of causes of the death from cancers in Japan and is fifth place next to lung, stomach, large intestine and liver in the mortality by the cancer of different parts.

A treatment for the pancreas cancer which is expected to be radical cure is only surgical resection, although approximately 10 to 20% of the whole pancreas cancer patients can actually undergo the radical resection, because many patients have been found with the condition of a progressive cancer (stage III+IV). A median survival period for each stage is approximately 12 to 30 months for Stage I and II, 9 to 11 months for Stage III and around 5 to 6 months for Stage IV, therefore the prognosis is very poor and it has been considered that there is a little possibility of the treatment for the patient, in particular who is unable to undergo the resection.

A gemcitabine has been used as a standard treatment for the progressive pancreas cancer, however other standard treatments have not been established, when the patient became refractory to the gemcitabine. The cases of good physical status are recognized in the patient with the progressive pancreas cancer when the patient became refractory to the gemcitabine, and it has been considered that a development of the effective treatment for such a patient group (pancreas cancer refractory to gemcitabine) is the important problem in the whole development of the therapeutics of pancreas cancer.

In recent years, it is reported that cells derived from pancreas cancer such as PANC-1, AsPC-1, BxPC-1 and KP-3 have strong tolerance to an extreme nutrient starvation state and that elimination of the tolerance may be a new biochemical approach in cancer therapy (Patent document 1).

It is reported that arctigenin was found to be effective as a material which can cancel the viability of tumor cells under undernutrition condition in the screening using pancreas cancer cell line PANC-1 (Non-patent document 1).

Here, in the Japanese Pharmacopoeia 15th edition, a burdock fruit is defined as a fruit of burdock, *Arctium lappa* Linne (Compositae). In addition, a burdock fruit is a herbal medicine prescribed for Gingyo-san, Kufugedoku-to, Shofusan and the like, and is classified into a primary material to be used as a pharmaceutical agent exclusively.

A burdock fruit contains approximately 7% of arctiin which is classified into lignan glycoside and approximately 0.6% of arctigenin which is an aglycone of arctiin. According to the above knowledge, it is expected that a burdock fruit extract containing arctigenin can be used as an anticancer agent for treating pancreas cancer.

PRIOR ART DOCUMENTS

Patent Document

Patent document 1: Japanese Kokai Publication No. 2002-065298

Non-Patent Document

Non-patent document 1: S. AwaLe, J. Lu, S. K. KaLauni, Y. Kurashima, Y. Tezuka, S. Kadota, H. Esumi, Cancer Res., 2006, 66 (3), 1751-1757),

SUMMARY OF THE INVENTION

Problem to be Solved by the Invention

The present invention is intended to provide a novel anticancer agent which has effect on a cancer.

Means to Solve the Problem

A burdock fruit which is known currently contains arctigenin at a low content of approximately 0.6%. In addition, it is hard to dissolve in water. Therefore, it has been extremely difficult to produce a burdock fruit extract containing arctigenin at high content by a conventional hot water extraction method.

In addition, it is desired to provide a burdock fruit extract containing a definite content of arctigenin as an active ingredient for use in treatment of pancreatic cancer and the like, however, it is difficult to control the conversion of arctiin into arctigenin so that a definite content of arctigenin which is hard to dissolve in water is contained in the production of the burdock fruit extract containing arctigenin at high content, as described above.

Furthermore, it is found that a burdock fruit extract containing arctigenin as a major active ingredient as well as containing a definite content of arctigenin and arctiin has a particularly excellent anticancer effect when it is used to treat pancreatic cancer and the like. Therefore, a method for production that can control the content of arctigenin and arctiin to a definite content is desired in the production of a burdock fruit extract containing arctigenin at high content. Particularly, a method to make it possible to produce a burdock fruit extract containing arctigenin and arctiin at a weight ratio of approximately 1:1 is desired.

As a result of the diligent investigation in order to solve the above problem, the inventors found a technique to make the content of arctigenin a definite content and a technique to adjust the content ratio of arctigenin to arctiin by adjusting the enzyme activity of beta-glucosidase endogenous in a burdock fruit as a raw material, the particle size of the cut burdock fruit, the temperature when enzymatically converting arctiin into arctigenin and the temperature in extracting arctigenin and arctiin from the burdock fruit.

In addition, the inventors observed the tumor reducing effect and confirmed the lowering of the tumor markers, when the agent is prepared at a dosage of 100 mg or more of arctigenin per day using the burdock fruit extract provided by those techniques and administered it to the patients with pancreas cancer. The present invention was made based on these surprising findings.

The present invention provides an anticancer agent containing arctigenin, wherein a dose of the arctigenin is 100 mg or more per day.

In addition, the present invention provides the anticancer agent further containing arctiin, wherein a dose of the arctiin is 100 mg or more per day.

In addition, the present invention provides the anticancer agent containing arctigenin and arctiin at weight ratio of arctigenin/arctiin=0.7 to 1.3.

In addition, the present invention provides the anticancer agent, wherein the arctigenin and the arctiin are derived from burdock fruit.

In addition, the present invention provides the anticancer agent for treating pancreas cancer that is refractory to treatment with gemcitabine.

In addition, the present invention provides an anti cancer stem cell agent containing arctigenin.

In addition, the present invention provides the anti cancer stem cell agent, wherein a dose of the arctigenin is 100 mg or more per day.

Effect of the Invention

The present invention can provide a novel anticancer agent having an effect on cancer.

EMBODIMENT FOR CARRYING OUT THE INVENTION

Figures 1A, 1B, 1C, 1D:
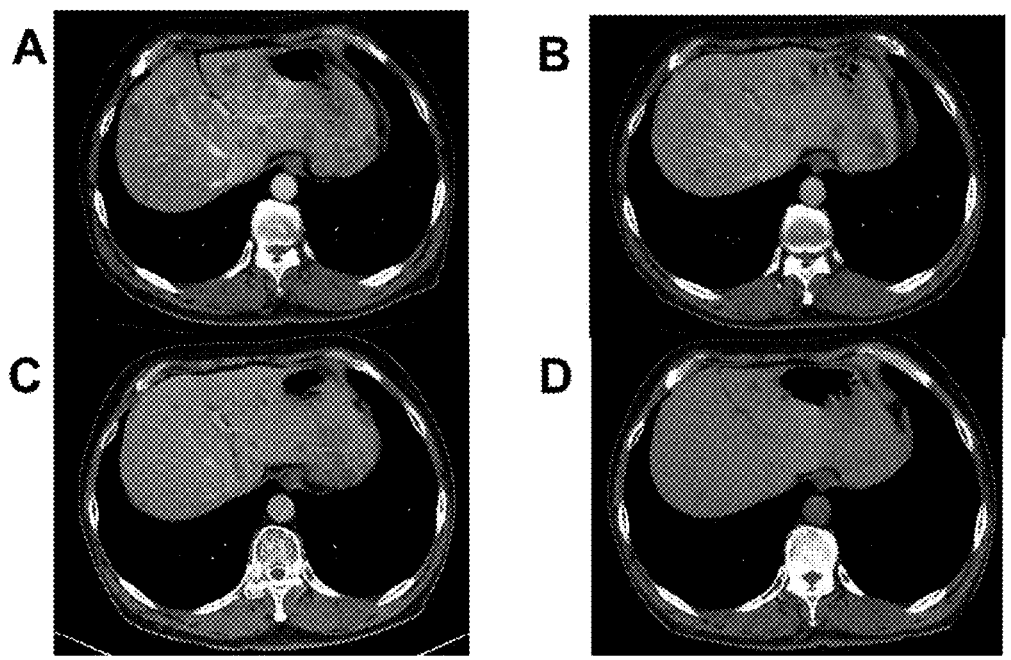
FIGS. 1A-1D show the results of the thoracoabdominal contrast CT before administering (A); one month later after the beginning of the administering (B); two month later (C); and three month later (D) the granules of an example of the present invention.
Figures 2A, 2B, 2C, 2D:
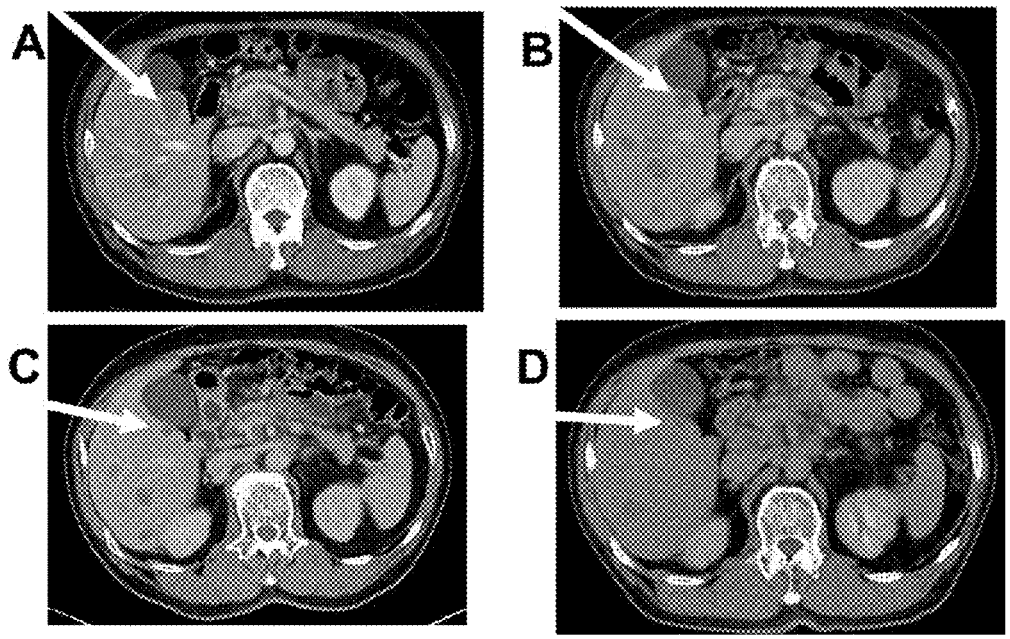
FIGS. 2A-2D show the results of thoracoabdominal contrast CT before administering (A); one month later after the beginning of the administering (B); two month later (C); and three month later (D) the granules of an example of the present invention.
Figures 3A, 3B, 3C, 3D:
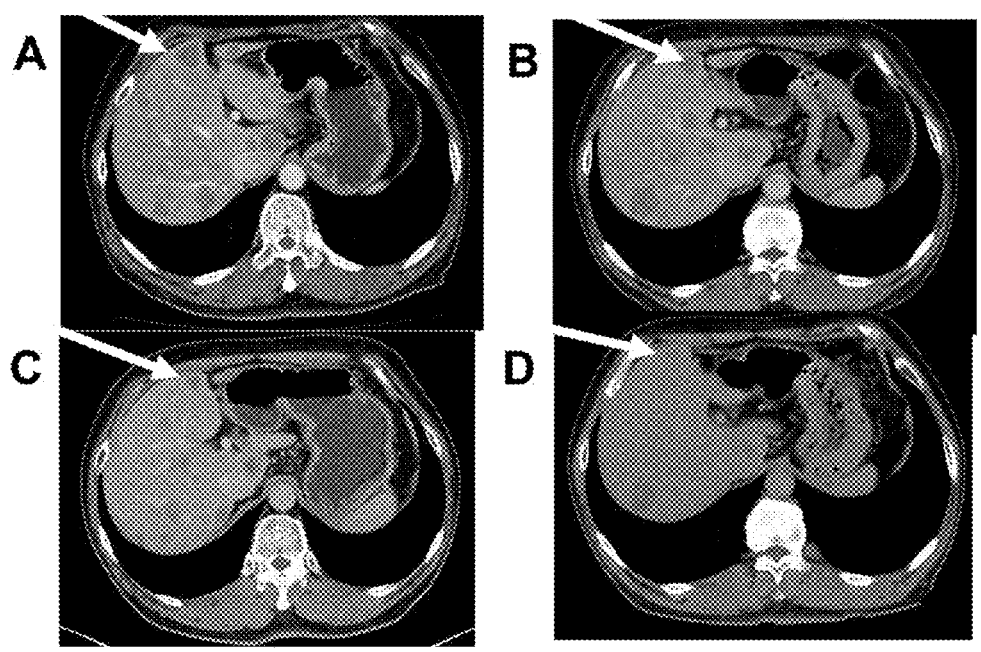
FIGS. 3A-3D show the results of thoracoabdominal contrast CT before administering (A); one month later after the beginning of the administering (B); two month later (C); and three month later (D) the granules of an example of the present invention.

The present invention is described below in detail. The disclosed conditions are examples, and the present invention is not limited to them.

An anticancer agent of the present invention contains arctigenin as an active ingredient so that a dose thereof is 100 mg or more per day. Arctigenin may be derived from a plant containing arctigenin, for example a burdock fruit. Therefore, the anticancer agent of the present ration may contain arctigenin as an active ingredient which is contained in an extract from a plant, for example a burdock fruit extract obtained from a burdock fruit.

Furthermore, the anticancer agent of the present invention may also contain arctiin as an active ingredient so that a dose thereof is 100 mg or more per day. Arctiin may be derived from a plant containing arctiin, for example a burdock fruit. Therefore, the anticancer agent of the present invention may contain arctiin as an active ingredient which is contained in an extract from a plant, for example, a burdock fruit extract obtained from a burdock fruit.

The anticancer agent of the present invention may also contain arctigenin and arctiin at weight ratio of arctigenin/arctiin=0.7 to 1.3 (mole ratio of 1.0 to 1.9). Arctigenin and arctiin may be derived from a plant containing arctigenin and arctiin, for example a burdock fruit. Therefore, the anticancer agent of the present invention may contain arctigenin and arctiin which are contained in an extract from a plant, for example a burdock fruit extract, at weight ratio of arctigenin/arctiin=0.7 to 1.3. Moreover, the anticancer agent may contain arctigenin so that a dose thereof is 100 mg or more per day and may contain arctiin so that a dose thereof is 100 mg or more per day.

The plant containing arctigenin and arctiin includes, but is not limited to, for example *Arctium lappa* L. (burdock) (sprout, leaf, rhizoma), *Carthamus tinctorius* (safflower), *Centaurea cyanus* (cornflower), *Cirsium vulgare, Cnicus benedictus* (*Centaurea benedicta*), *Cynara cardunculus* (cardoon), *Onopordum acanthium*, thistle (Aniurokoazami), *Forsythia×intermedia, Forsythia ovata, Forsythia suspensa* (weeping forsythia), *Forsythia viridissima, Sesamum indicum* (sesame), *Ipomoea cairica, Polygala chinensis, Trachelospermum asiaticum* var. *glabrum, Trachelospermum asiaticum, Trachelospermum gracilipes* var. *liukiuense, Trachelospermum gracilipes, Trachelospermum jasminoides* var. *jasminoides, Trachelospermum jasminoides* var. *pubescens, Wikstroemia indica, Persicaria orientalis* (*Polygonum orientate*), *Cerasus jamasakura* (wild cherry tree), *Arabidopsis thaliana*, amaranth, *Juglans* (walnut), *Avena sativa* (oat), *Triticum spelta*, soft wheat, *Cupressus lusitanica, Torreya nucifera* (Japanese nutmeg) and the like. Among them, burdock and weeping forsythia which have high arctigenin content are preferable.

In the present invention, a burdock fruit extract provided by using the method for producing a burdock fruit extract described below can be used when arctigenin and arctiin are derived from a burdock fruit. Therefore, the productivity at the time of the manufacture can be improved and the anticancer agent can be prepared easily at a low cost. In addition, when a plant except a burdock fruit is used, the extract containing arctigenin and arctiin can be also obtained easily by using method for producing described below.

The extract powder obtained by using the method for producing a burdock fruit extract described below contains arctigenin and arctiin at weight ratio of arctigenin/arctiin=0.7 to 1.3. Therefore, the extract powder obtained by using the method for producing a burdock fruit extract can be used as an anticancer agent of the present invention having a superior anticancer effect in comparison with the conventional burdock fruit extract.

Furthermore, the anticancer agent of the present invention can include any components. For example, the anticancer agent of the present invention can be provided in a form including a pharmaceutically acceptable base, a carrier, an excipient, a disintegrator, a lubricant, a coloring agent and the like.

Examples of the carrier and the excipient used for the anticancer agent include lactose, glucose, saccharose, mannitol, dextrin, potato starch, corn starch, calcium carbonate, calcium phosphate, calcium sulfate, crystalline cellulose and the like.

In addition, examples of the binder include starch, gelatin, syrup, gum tragacanth, polyvinyl alcohol, polyvinyl ether, polyvinyl pyrrolidone, hydroxypropyl cellulose, methyl cellulose, ethyl cellulose, carboxymethyl cellulose and the like.

In addition, examples of the disintegrator include starch, agar, gelatin powder, crystalline cellulose, calcium carbonate, sodium hydrogen carbonate, sodium alginate, sodium carboxymethylcellulose, carboxymethylcellulose calcium and the like.

In addition, examples of the lubricant include magnesium stearate, hydrogenated vegetable oil, talc, macrogol and the like. In addition, any coloring agent permitted to be added to a pharmaceutical agent can be used as the coloring agent.

In addition, if necessary, the anticancer agent may be coated with one or more layers using saccharose, gelatin, purified shellac, gelatin, glycerin, sorbitol, ethyl cellulose, hydroxypropyl cellulose, hydroxypropyl methylcellulose, polyvinylpyrrolidone, cellulose acetate phthalate, hydroxypropyl methylcellulose phthalate, methyl methacrylate, methacrylic acid polymer and the like. In addition, if necessary, a pH regulator, a buffer, a stabilizer, a solubilizer and the like may be added.

In addition, the anticancer agent can be provided as a formulation in any form. For example, as an orally administered formulation, the anticancer agent can be a tablet such as a sugar-coated tablet, a buccal tablet, a coated tablet or a chewable tablet, a capsule such as a troche, a pill, a powder or a soft capsule, a granule, a suspension, an emulsion, a syrup such as a dry syrup or a liquid formulation such as an elixir.

Alternatively, the anticancer agent can be a formulation for administration such as intravenous injection, subcutaneous injection, intraperitoneal injection, intramuscular injection, percutaneous administration, nasal administration, pulmonary administration, enteral administration, intraoral administration and transmucosal administration for parenteral administration. For example, it can be an injectable solution, a percutaneous absorption tape, an aerosol or a suppository. In addition, the extract powder can be a masked formulation or a film coated agent coated with a coating agent, because the extract powder has a special acrid taste.

Meanwhile, the extract powder provided by using the method for producing a burdock fruit extract described below can be used as it is.

The anticancer agent of the present invention may be prepared by mixing the purified arctigenin and other components or may be prepared by using the burdock fruit extract prepared by the method describe below.

The burdock fruit extract is prepared through a step of cutting a herbal medicine, an extraction step (an enzymatic conversion step and an extraction step by an organic solvent), a separating step of solid and liquid, a concentrating step and a drying step.

(Process of Cutting Herbal Medicine)

In the method for producing the burdock fruit extract used for the anticancer agent of the present invention, the burdock fruit which is a raw material is cut into a size suitable for the extraction. The herbal medicine which is a raw material is various parts of plant, mineral or animal or the like with various kinds of size, shape and hardness, and have to be cut according to the characteristic. The burdock fruit can be cut using any means well known to those skilled in the art. For example, a commercial cutting machine can be used.

In the method for producing the burdock fruit extract used for the anticancer agent of the present invention, the activity of beta-glucosidase which is an enzyme inherent in the burdock fruit can be measured beforehand for the selection of the burdock fruit suitable for the production of the present invention.

For a method for measuring the activity of beta-glucosidase, for example, a ground product of a burdock fruit is acted on p-nitrophenyl-beta-D-glucopyranoside ($C_{12}H_{15}NO_8$: molecular weight 301.25) (manufactured by SIGMA-ALDRICH) as a substrate to generate p-nitrophenol, and the enzyme activity can be measured by measuring the variation of the absorbance at 400 nm. For the unit representing the enzyme activity, the enzyme level generating 1 µmol of p-nitrophenol per minute can be expressed as 1 unit (U).

In order to provide the burdock fruit extract containing arctigenin and arctiin at a weight ratio of arctigenin/arctiin=0.7 to 1.3, a burdock fruit can be used wherein the activity of the beta-glucosidase which is inherent in the burdock fruit is 0.4 U/g or more, preferably 1 U/g or more. If the activity is lower than 0.4 U/g, the hydrolysis will be insufficient and the weight ratio of arctigenin will decrease, and therefore the desired burdock fruit extract cannot be obtained efficiently.

In addition, in the method for producing the burdock fruit extract used for the anticancer agent of the present invention, a burdock fruit which is cut into an arbitrary particle size can be used. The smaller the particle size of the cut burdock fruit is, the more the enzymatic conversion may be promoted and the yield of the extract may be increased. On the other hand, if the particle size is too small, the control of the process may become difficult because the enzymatic conversion is too fast, and a trouble may occur for the accurate solid-liquid separation in the subsequent step.

In order to provide the burdock fruit extract containing arctigenin and arctiin at a weight ratio of arctigenin/arctiin=0.7 to 1.3, as shown in the following EXAMPLES, the burdock fruit is cut into a particle size of 9.5 mm or less, for example, the burdock fruit is cut so that all of the burdock fruit particles pass through a sieve of 9.5 mm.

In addition, in order to provide the burdock fruit extract containing arctigenin and arctiin at a weight ratio of arctigenin/arctiin=0.7 to 1.3, it is desirable that the burdock fruit is cut so that all of the burdock fruit particles pass through a sieve of 9.5 mm and, for example, 60 to 100% are distributed on a sieve of 0.85 mm, and more preferably, 65 to 80% are distributed on a sieve of 0.85 mm.

(Extraction Step)

The extraction step is the most important step in terms of quality among steps of producing a powder of the herbal medicine extract. Due to this extraction step, the quality of the powder of the herbal medicine extract is decided. In the method for producing the burdock fruit extract of the present invention, two stages of the enzymatic conversion step and the extraction step using an organic solvent are carried out to extract the burdock fruit extract.

(Enzymatic Conversion Step)

The enzymatic conversion step is an important step in the method for producing the burdock fruit extract used for the anticancer agent of the present invention. The enzymatic conversion step is a step of enzymatically converting arctiin contained in the burdock fruit into arctigenin by beta-glucosidase which is an enzyme in the burdock fruit.

Specifically, the cut burdock fruit prepared by the above steps is retained at an appropriate temperature to make the beta-glucosidase function and progress the reaction from arctiin to arctigenin. For example, an arbitrary solution such as water is added to the cut burdock fruit and stirred at a temperature such as around 30° C., and thereby the burdock fruit can be retained at an arbitrary temperature.

In order to provide the burdock fruit extract containing arctigenin and arctiin at a weight ratio of arctigenin/arctiin=0.7 to 1.3, the cut burdock fruit is retained at a temperature of around 30° C., such as a temperature between 20 to 50° C.

If it is lower than 20° C., the hydrolysis will be insufficient and the weight ratio of arctigenin will decrease, and therefore the desired burdock fruit extract cannot be obtained efficiently. On the other hand, if it is er than 50° C., the enzyme will be deactivated and the weight ratio of arctigenin will be decrease, and therefore the desired burdock fruit extract cannot be obtained efficiently.

In addition, the length of time for retaining is not limited particularly, as far as the burdock fruit is retained at the above temperature, and for example, it can be retained for approximately 30 minutes. By retaining at 20 to 50° C., an appropriate amount of arctiin is enzymatically converted into arctigenin regardless of the length of time for retaining, and the burdock fruit extract containing arctigenin and arctiin at a weight ratio of approximately 1:1 can be obtained.

(Extraction Step Using Organic Solvent)

The extraction step using an organic solvent is a step of extracting arctigenin and arctiin from the burdock fruit using any appropriate organic solvent. In other words, it is a step of extracting the burdock fruit extract by adding an appropriate solvent in the state in which the content of arctigenin is increased after the above step of enzymatic conversion. For example, an appropriate solvent is added to the burdock fruit extract, and the mixture is heated and stirred for an appropriate length of time to extract the burdock fruit extract. In addition, the burdock fruit extract can be extracted using any extraction method well known to those skilled in the art such as a method of heating to reflux, a method of drip extraction, a method of dipping extraction or a method of pressurized extraction, other than the heating and stirring method.

Because arctigenin is hardly soluble in water, the yield of arctigenin can be improved by adding an organic solvent. Any organic solvent can be used as the organic solvent. For example, alcohols such as methanol, ethanol and propanol as well as acetone can be used. In consideration of safety, ethanol is preferably used as the organic solvent in the method for producing the burdock fruit extract used for the anticancer agent of the present invention.

If the burdock fruit extract is extracted by the heating and stirring, the heating and stirring can be carried out at any temperature, however, the burdock fruit is retained at a temperature of 80° C. or more, such as a temperature between 80 to 90° C. in order to provide the burdock fruit extract containing arctigenin and arctiin at a weight ratio of arctigenin/arctiin=0.7 to 1.3.

In addition, the length of time for the heating and stirring is not limited particularly, as far as the burdock fruit is heated and stirred at the above temperature, and arctigenin and arctiin can be extracted from the burdock fruit into the solvent by the heating and stirring the burdock fruit for approximately 30 minutes, such as 30 to 60 minutes.

The longer the length of time for the heating and stirring is, the more the yield of arctigenin and arctiin is improved. However, if the length of time for the heating and stirring is longer, larger amounts of unnecessary oils and fats begin to dissolve, and the load of the concentrating step becomes larger. Therefore, the length of time for the heating and stirring should be determined appropriately according to the situation.

In addition, the larger the amount of ethanol is, the higher the solubility of arctigenin and arctiin and the more the yield of arctigenin and arctiin is improved. However, if the amount of ethanol is larger, larger amounts of unnecessary oils and fats begin to dissolve, and the load of the concentrating step becomes larger. Therefore, the added amount should be determined appropriately according to the situation. Note that the burdock fruit extract can be sterilized and pasteurized simultaneously by the heating and stirring in this step.

(Separating Step of Solid and Liquid)

The step of separating solid and liquid is a step of separating the burdock fruit subjected to the extraction from the extract liquid. The solid-liquid separation can be carried out using any method well known to those skilled in the art. The method for solid-liquid separation includes, for example, a filtration method, a sedimentation method and a centrifugal separation method. Industrially, a centrifugal separation method is desirable.

(Concentrating Step)

The concentrating step is a step of removing the solvent from the burdock fruit extract liquid prior to drying. The removal of the solvent from the burdock fruit extract liquid can be carried out using any method well known to those skilled in the art.

However, it is preferable for the extract liquid from the burdock fruit provided by the above steps not to be exposed furthermore to a high temperature for a long time.

For example, the burdock fruit extract liquid can be concentrated by using a decompression concentration method without being exposed to a high temperature for a long time.

The burdock fruit extract liquid can be concentrated until the burdock fruit extract with a desired concentration can be obtained.

For example, it is desirable to concentrate the extract liquid to the extent that the drying can be carried out appropriately in the following drying step. Alternatively, when the burdock fruit extract is dried and formulated into a powder in the following steps, it is desirable to concentrate the extract liquid until appropriate properties of the formulation can be obtained.

Because arctigenin and arctiin are hardly soluble in water, a large quantity of arctigenin and arctiin may adhere to the inside of the manufacturing apparatus in the following drying step, and thereby the final yield may be largely decreased. Therefore, dextrin can be added to the burdock fruit extract liquid provided in the concentrating step in order to prevent the adhesion of arctigenin and arctiin to the manufacturing apparatus. For example, the amount of the dextrin to be added is preferably around 15 to 30% relative to the solid content of the concentrated liquid.

(Drying Step)

It is a step of finishing the burdock fruit extract provided by the above steps into a powder form. The drying can be carried out using any method well known to those skilled in the art. For example, freeze-drying and spray drying are known as a drying method, and it is common to use the former for laboratory scale production and the latter for mass production.

The burdock fruit extract containing arctigenin and arctiin at a weight ratio of arctigenin/arctiin=0.7 to 1.3 can be provided by the above production process. The method for producing the burdock fruit extract must include a step of enzymatic conversion at a temperature from 20° C. to 50° C., however it is not necessary to include all of the other steps.

In addition, the burdock fruit extract containing arctigenin at high concentration can be provided easily at low cost by using the above-mentioned production process. Therefore, the anticancer agent of the present invention can be prepared easily at low cost by using the burdock fruit extract provided by using this method.

In addition, the arctigenin concentration of the burdock fruit extract provided by the above-mentioned production process is high, so that the total weight of the anticancer agent per day can be reduced in comparison with the case when the conventional burdock fruit extract is used. Therefore, the burden of a patient can be reduced.

Note that, the present invention also provides a method for producing a burdock fruit extract containing arctigenin and arctiin at a weight ratio of arctigenin/arctiin=0.7 to 1.3 (mole ratio of 1.0 to 1.9), including steps of: cutting a burdock fruit, and converting arctiin which is inherent in the burdock fruit into arctigenin by enzymatic conversion by beta-glucosidase which is inherent in the burdock fruit, wherein the enzymatic conversion includes a reaction at a temperature from 20° C. to 50° C.

In addition, the present invention provides the method for producing the burdock fruit extract, wherein the burdock fruit is cut into a particle size from 0.85 mm to 9.5 mm in the step of cutting.

Furthermore, the present invention provides the method for producing the burdock fruit extract, wherein the enzyme activity of the beta-glucosidase which is inherent in the burdock fruit is 0.4 U or more per 1 g of the burdock fruit.

In addition, the present invention provides the method for producing the burdock fruit extract, including a step of extracting an extract containing arctigenin and arctiin by adding an organic solvent after the step of enzymatic conversion.

In addition, the present invention provides the method for producing the burdock fruit extract, wherein the organic solvent is ethanol.

In addition, the present invention provides the method for producing the burdock fruit extract, wherein the extract is extracted at approximately 80° C. in the extraction step.

Furthermore, the present invention provides a burdock fruit extract containing arctigenin and arctiin at weight ratio of arctigenin/arctiin=0.7 to 1.3 which is provided by the above method.

Furthermore, the present invention provides an anticancer agent containing the burdock fruit extract containing arctigenin and arctiin at weight ratio of arctigenin/arctiin=0.7 to 1.3 which is provided by the above method.

The present invention can provide an anticancer agent with antitumor effect which contains arctigenin so that a dose thereof is 100 mg or more per day. Moreover, the present invention can provide an anticancer agent containing arctigenin and arctiin at weight ratio of arctigenin/arctiin=0.7 to 1.3. Stable inhibition of the growth of a tumor and the antitumor effect can be expected by administering the anticancer agent of the present invention to a patient suffering from cancer, for example pancreas cancer. In addition, the anticancer agent of the present invention can be used as a therapeutic agent for pancreas cancer to treat pancreas cancer that is refractory to treatment with gemcitabine.

In addition, test example 7 below showed that the toxicity of the granule containing arctigenin and arctiin was very low. Therefore, the anticancer agent of the present invention can provide high anticancer effect with very few side effects.

In addition, test examples 8 and 9 below showed that arctigenin has an effect of killing pancreas and hepatic cancer stem cell. Therefore, it is suggested that arctigenin demonstrates anticancer activity to solid cancer by acting on and killing not only tumor body but also cancer stem cell. Moreover, it showed that arctigenin has an anticancer effect by killing not only pancreas cancer stem cell but also other cancerous cancer stem cell. Therefore, the present invention provides an anticancer agent for the treatment of various cancers.

The present invention also provides an anti cancer stem cell agent containing arctigenin. A cancer stem cell refers to a cell having a property of a stem cell among cancer cells.

The anti cancer stem cell agent of the present invention can be composed same as the anticancer agent of the present invention described above. Therefore, the anti cancer stem cell agent may contain arctigenin so that a dose thereof is 100 mg or more per day. In addition, the anti cancer stem cell agent may further contain arctiin or may contain arctiin so that a dose thereof is 100 mg or more per day. The anti cancer stem cell agent may contain arctigenin and arctiin at a weight ratio of arctigenin/arctiin=0.7 to 1.3. Arctigenin and arctiin may be derived from a plant containing arctigenin and arctiin, for example, burdock fruit.

The test examples 8 and 9 below showed that arctigenin has an effect of killing cancer stem cell selectively, particularly under the nutrition starvation condition which is close to the environment around cancer cell. Therefore, the anti cancer stem cell agent of the present invention can inhibit the growth of cancer cell by killing cancer stem cells and therefore can be preferably used as an anticancer agent.

EXAMPLES

Test Examples

The influence on arctigenin/arctiin ratio (weight ratio) caused by the enzyme activity of the burdock fruit and the condition of the enzymatic conversion (temperature and length of time), namely, the cause and effect relationship of both, was verified.

(Measurement of Enzyme Activity)

Burdock fruits differing in production regions and lots were pulverized by a Wiley mill, and 0.1 g of each pulverized burdock fruit was diluted with 10 mL of water as a sample solution.

As a substrate solution, water was added to 0.15 g of p-nitrophenyl-beta-D-glucopyranoside and the volume was fixed at 25 mL to prepare a 20 mmol/L aqueous solution of p-nitrophenyl-beta-D-glucopyranoside. 0.5 mL of the 20 mmol/L aqueous solution of p-nitrophenyl-beta-D-glucopyranoside was added to 1 mL of a 0.1 mol/L acetate buffer to prepare a cocktail and the cocktail was preheated at 37° C. for approximately 5 minutes.

0.5 mL of the sample solution was added to the cocktail and they were reacted at 37° C. for 15 minutes, and then 2 mL of a 0.2 mol/L aqueous solution of sodium carbonate as a reaction stop solution was added to stop the reaction. The absorbance of this solution at 400 nm was measured and the enzyme activity was calculated based on the variation from the blank solution that was not subjected to the enzymatic reaction using the following formula.

Enzyme activity (U/g)=(Absorbance of the sample solution−Absorbance of the blank solution)×4 mL×1/18.1 (Millimolar molecular extinction coefficient of p-nitrophenol under the above measurement condition: $cm^2/\mu mol$)×1/Light path length (cm)×1/Reaction time (minute)×1/0.5 mL×1/Sample solution level (g/mL)

It was confirmed that the enzyme activity of each burdock fruit was 0.12 to 8.23 U/g as shown in Table 1.

Test Example 1

7 mL of water was added to 1 g of the cut burdock fruit having an enzyme activity of 0.12, 0.27 or 0.40 U/g (Samples 1 to 3), and the temperature conditions for the enzymatic reaction were set to 15° C. and 20° C. and the reaction time at respective reaction temperature was set to 30 minutes. Ethanol was added after the reaction, and the extraction was carried out at 80° C., arctigenin and arctiin of the obtained extract were quantitated, and the weight ratio of arctigenin/arctiin was calculated. The results are shown in Comparative Examples 1 to 2 and Example 1 of Table 1.

In Sample 3 having an enzyme activity of 0.40 U/g, a burdock fruit extract with arctigenin/arctiin (weight ratio)=0.82 was obtained when the temperature of the enzymatic reaction was 20° C. and the reaction time was 30 minutes.

On the other hand, arctigenin/arctiin (weight ratio) was 0.69 when the temperature of the enzymatic reaction was 15° C. and the reaction time was 30 minutes, therefore the temperature of the enzymatic reaction is preferably 20° C. or more.

In addition, Samples 1 and 2 having an enzyme activity of less than 0.40 U/g could not satisfy arctigenin/arctiin (weight ratio)=0.70 or more even if the temperature of the enzymatic reaction was 20° C., therefore the enzyme activity of the burdock fruit is preferably 0.40 U/g or more.

Test Example 2

7 mL of water was added to 1 g of the cut burdock fruit having an enzyme activity of 4.03 U/g (Sample 5), the temperature conditions for the enzymatic reaction were set to 30° C., 40° C., 50° C. and 60° C. and the reaction time at respective reaction temperature was set to 15 minutes and 30 minutes (only 30° C. and 60° C.). The extraction was carried out using ethanol after the reaction, and arctigenin and arctiin of the obtained extract were quantitated, and the weight ratio of arctigenin/arctiin was calculated.

The results are shown in Example 3 of Table 1. The burdock fruit extracts with arctigenin/arctiin (weight ratio)=0.7 when the temperature of the enzymatic reaction was 30° C. and the reaction time was 15 minutes, with arctigenin/arctiin (weight ratio)=1.0 when the temperature of the enzymatic reaction was 30° C. and the reaction time was 30 minutes, with arctigenin/arctiin (weight ratio)=1.2 when the temperature of the enzymatic reaction was 40° C. and the reaction time was 15 minutes, and with arctigenin/arctiin (weight ratio)=1.2 when the temperature of the enzymatic reaction was 50° C. and the reaction time was 15 minutes, were obtained.

On the other hand, arctigenin/arctiin (weight ratio) was 0.4 when the temperature of the enzymatic reaction was 60° C. and the reaction time was 15 minutes and arctigenin/arctiin (weight ratio) was 0.5 when the temperature of the enzymatic reaction was 60° C. and the reaction time was 30 minutes. Based upon the foregoing, the temperature of the enzymatic reaction is preferably less than 60° C.

Test Example 3

7 mL of water was added to 1 g of the cut burdock fruit having an enzyme activity of 1.42 U/g (Sample 4), the temperature condition for the enzymatic reaction was set to 25° C. and the reaction time was set to 10 minutes and 30 minutes. The extraction was carried out using ethanol after the reaction, and arctigenin and arctiin of the obtained extract were quantitated, and the weight ratio of arctigenin/arctiin was calculated.

The results are shown Example 2 of Table 1. The burdock fruit extracts with arctigenin/arctiin (weight ratio)=0.74 when the temperature of the enzymatic reaction was 25° C. and the reaction time was 10 minutes and with arctigenin/arctiin (weight ratio)=0.85 when the temperature of the enzymatic reaction was the same and the reaction time was 30 minutes, were obtained.

Based upon the foregoing, even if the enzyme activity was 1.42 U/g, desired results were able to be obtained.

TABLE 1

| | | | Comparative example 1 | Comparative example 2 | Example 1 | Example 2 | Example 3 | Example 4 | Example 5 |
|---|---|---|---|---|---|---|---|---|---|
| | sample | | Sample 1 | Sample 2 | Sample 3 | Sample 4 | Sample 5 | Sample 6 | Sample 7 |
| | enzyme activity (U/g) | | 0.12 | 0.27 | 0.40 | 1.42 | 4.03 | 7.82 | 8.23 |
| arctigenin/ | 15° C. | 30 min | 0.26 | 0.50 | 0.69 | — | — | — | — |
| arctiin | 20° C. | 30 min | 0.23 | 0.60 | 0.82 | — | — | — | — |
| (weight | 25° C. | 10 min | — | — | — | 0.74 | — | — | — |
| ratio) | | 30 min | — | — | — | 0.85 | — | — | — |
| | 30° C. | 15 min | — | — | — | — | 0.70 | — | — |
| | | 30 min | — | — | — | — | 1.00 | 0.93 | 0.89 |
| | 40° C. | 15 min | — | — | — | — | 1.20 | — | — |
| | | 30 min | — | — | — | — | — | — | — |
| | 50° C. | 15 min | — | — | — | — | 1.20 | — | — |
| | | 30 min | — | — | — | — | — | — | — |
| | 60° C. | 15 min | — | — | — | — | 0.40 | — | — |
| | | 30 min | — | — | — | — | 0.50 | — | — |

Example 6

Production of Burdock Fruit Extract 1

A burdock fruit (enzyme activity was 8.23 U/g) was cut, and all the particles passed through a sieve of 9.5 mm were further passed through a sieve of 0.85 mm and confirmed that 75% of them were remained. 80 kg of this chopped burdock fruit was added to 560 L of water kept warm at 29 to 33° C. and stirred for 30 minutes. Then, 265 L of ethanol was added and the temperature was raised to 85° C. and the mixture was further heated to reflux for 60 minutes. This solution was centrifuged and a burdock fruit extract liquid was obtained. This operation was repeated two times and the obtained extract liquids were combined, and vacuum concentration was carried out, and 20% of dextrin relative to the solid content of the extract was added and the mixture was spray dried. The arctigenin content and the arctiin content were 6.2% and 7.1% respectively, and the burdock fruit extract powder with arctigenin/arctiin (weight ratio)=0.89 (containing 20% of dextrin) was obtained.

Example 7

Production of Burdock Fruit Extract 2

A burdock fruit (enzyme activity was 8.23 U/g) was cut, and all the particles passed through a sieve of 9.5 mm were further passed through a sieve of 0.85 mm and confirmed that 75% of them were remained. After 80 kg of this chopped burdock fruit was added to 560 L of water kept warm at 30 to 33° C. and stirred for 30 minutes, 265 L of ethanol was added and the temperature was raised to 85° C., and the mixture was further heated to reflux for 30 minutes. This solution was centrifuged and a burdock fruit extract liquid was obtained. This operation was repeated two times and the obtained extract liquids were combined, and vacuum concentration was carried out, and 20% of dextrin relative to the solid content of the extract was added and the mixture was spray dried. The arctigenin content and the arctiin content were 6.0% and 6.8% respectively, and the burdock fruit extract powder with arctigenin/arctiin (weight ratio)=0.87 (containing 20% of dextrin) as obtained.

Example 8

Production of Burdock Fruit Extract 3

A burdock fruit (enzyme activity was 7.82 U/g) was cut, and all the particles passed through a sieve of 9.5 mm were further passed through a sieve of 0.85 mm and confirmed that 75% of them were remained. 80 kg of this chopped burdock fruit was added to 560 L of water kept warm at 30 to 32° C. and stirred for 40 minutes, and after 60 minutes, 258 L of ethanol was added and the temperature was raised to 85° C., and the mixture was further heated to reflux for 30 minutes. This solution was centrifuged and a burdock fruit extract liquid was obtained. This operation was repeated two times and the obtained extract liquids were combined, and vacuum concentration was carried out, 20% of dextrin relative to the solid content of the extract was added and the mixture was spray dried. The arctigenin content and the arctiin content were 6.2% and 6.7% respectively, and the burdock fruit extract powder with arctigenin/arctiin (weight ratio)=0.93 (containing 20% of dextrin) was obtained.

Example 9

Production of Burdock Fruit Extract 4

A burdock fruit (enzyme activity was 7.82 U/g) was cut, and all the particles passed through a sieve of 9.5 mm were further passed through a sieve of 0.85 mm and confirmed that 75% of them were remained. After 80 kg of this chopped burdock fruit was added to 560 L of water kept warm at 30 to 32° C. and stirred for 30 minutes, 253 L of ethanol was added and the temperature was raised to 85° C. and the mixture was further heated to reflux for 40 minutes. This solution was centrifuged and a burdock fruit extract liquid was obtained. This operation was repeated two times and the obtained extract liquids were combined, and vacuum concentration was carried out, 25% of dextrin relative to the solid content of the extract was added and the mixture was spray dried. The arctigenin content and the arctiin content were 6.4% and 7.2% respectively, and the burdock fruit extract powder with arctigenin/arctiin (weight ratio)=0.89 (containing 25% of dextrin) was obtained.

TABLE 2

| | | Example 6 | Example 7 | Example 8 | Example 9 |
|---|---|---|---|---|---|
| burdock fruit | enzyme activity | 8.23 | 8.23 | 7.82 | 7.82 |
| step of cutting | particle size (mm) | 0.85-9.5 | 0.85-9.5 | 0.85-9.5 | 0.85-9.5 |
| step of enzymatic conversion | temperature (° C.) | 29 to 33° C. | 30 to 33° C. | 30 to 32° C. | 30 to 32° C. |
| | time (min) | 30 min | 30 min | 40 min | 30 min |
| extraction step | solvent | ethanol | ethanol | ethanol | ethanol |
| | temperature (° C.) | 85° C. | 85° C. | 85° C. | 85° C. |
| | time (min) | 60 min | 30 min | 30 min | 40 min |
| step of separating solid and liquid | | Centrifugal separation | Centrifugal separation | Centrifugal separation | Centrifugal separation |
| concentrating step | | vacuum concentration | vacuum concentration | vacuum concentration | vacuum concentration |
| drying step | | spray drying | spray drying | spray drying | spray drying |
| arctigenin/arctiin (weight ratio) | | 0.89 | 0.87 | 0.93 | 0.89 |

From the results of the above Examples 6 to 9, it was found that a burdock fruit extract with the content of arctigenin:arctiin (weight ratio)=approximately 1:1 can be provided by enzymatically converting arctiin into arctigenin at approximately 30° C. in the step of enzymatic conversion. A reaction caused by an enzyme usually progresses dependent on the temperature and the length of time, however, it was found that, at the above temperature, a burdock fruit extract with the content of arctigenin:arctiin (weight ratio) =approximately 1:1 can be obtained regardless of the length of time for the enzymatic conversion.

In addition, from the results of the above Examples 6 to 9, it was found that a burdock fruit extract with the content of arctigenin:arctiin (weight ratio)=approximately 1:1 can be obtained by raising the temperature to approximately 85° C. for heating to reflux in the step of heating to reflux. Usually, when the heating to reflux is carried out to obtain an extract, the amount of the ingredient within the extract changes dependent on the temperature and the length of time, however, it was found that, at the above temperature, a burdock fruit extract with the content of arctigenin:arctiin (weight ratio)=approximately 1:1 can be obtained regardless of length of time for heating to reflux.

Example 10

Granule Formulated with Burdock Fruit Extract Powder

| | |
|---|---|
| (1) Burdock fruit extract powder of Example 7 | 33.3% |
| (2) Lactose | 65.2% |
| (3) Hydroxypropyl cellulose | 1.5% |
| Total | 100% |

(Method for Production)

A granule was produced according to the paragraph of Granule in the General Rules for Preparations of "Japanese Pharmacopoeia". That is, the ingredients from (1) to (3) described in the above list were taken and produced into a granule form. Each 1.5 g of the granular material was packed into an aluminum laminate film, and a granule containing 0.5 g of the burdock fruit extract powder per one package was obtained.

Example 11

Granule Formulated with Burdock Fruit Extract Powder

| | |
|---|---|
| (1) Burdock fruit extract powder of Example 7 | 66.7% |
| (2) Lactose | 30.3% |
| (3) Hydroxypropyl cellulose | 3.0% |
| Total | 100% |

(Method for Production)

A granule was produced according to the paragraph of Granule in the General Rules for Preparations of "Japanese Pharmacopoeia". That is, the ingredients from (1) to (3) described in the above list were taken and produced into a granule form. Each 3.0 g of the granular material was packed into an aluminum laminate film, and a granule containing 2 g of the burdock fruit extract powder per one package was obtained.

Example 12

Tablet Formulated with Burdock Fruit Extract Powder

| | |
|---|---|
| (1) Burdock fruit extract powder of Example 7 | 37.0% |
| (2) Crystalline cellulose | 45.1% |
| (3) Carmellose calcium | 10.0% |
| (4) Crospovidone | 3.5% |
| (5) Hydrous silicon dioxide | 3.4% |
| (6) Magnesium stearate | 1.0% |
| Total | 100% |

(Method for Production)

A tablet was produced according to the paragraph of Tablet in the General Rules for Preparations of "Japanese Pharmacopoeia". That is, the ingredients from (1) to (6) described in the above list were taken and produced into the tablet.

Test Example 4

The effect on pancreas cancer was examined using the granule of Example 10.

The patient (53 years old, man), who had been confirmed that he has an adenocarcinoma (including adenosquamous carcinoma) by histopathology and then Gemcitabine+S-1 therapy had been carried out as a pre-treatment during one year and three months, and then Best-response had been a Partial Response (PR) and then the cancer had finally acquired resistance to Gemcitabine+S-1 therapy and then became PD (Progressive Disease), was targeted. The 7.5 g (5 packs) of the granule of Example 10 (containing 2.5 g of burdock fruit extract powder) was daily administered orally to this patient after breakfast once a day.

Note that, 1 g of the burdock fruit extract powder which was contained in the granule used in this test contained 59.4 mg of arctigenin and 68.5 mg of arctiin. In other words, 148.5 mg of arctigenin and 171.25 mg of arctiin were administered to the patient per day.

FIGS. 1A-1D to FIGS. 3A-3D show the images of a thoracoabdominal contrast CT in this patient before administering the granules (A); one month later after the beginning of the administering (B); two month later (C); and three month later (D). The evaluation of the tumor reducing effect was carried out time dependently from these images based on new guidelines for therapy effect evaluation on solid cancer (RECIST guideline (version1.1)). As a result, the tumor reducing effect was confirmed as shown in arrows in FIGS. 2A-2D and 3A-3D. On the other hand, no serious side effect after administration of the granule of Example 10 was seen in the above patient.

Furthermore, quantity of tumor markers CA19-9 and CEA before and after administration of the granule was examined. As a result, the drop of the tumor markers CA19-9 and CEA after administration of the granule was confirmed as shown in Table 3.

TABLE 3

| | before administering | one month later after administering | two month later after administering | three month later after administering |
|---|---|---|---|---|
| CA19-9 (U/mL) | 69.7 | 172.5 | 123 | 100.6 |
| CEA (ng/mL) | 66.4 | 224.1 | 114.8 | 98.3 |

Therefore, it has been shown that the anticancer agent of the present invention is effective to pancreas cancer. Especially, it is shown that it is effective to pancreas cancer that is refractory to treatment with gemcitabine. It has not been known conventionally that the composition of the present invention is effective to pancreas cancer when administrated, and additionally, the effect could not be achieved easily unless the composition was actually administered to a person.

In addition, it can be expected that the anticancer agent of the present invention is effective to not only pancreas cancer but also hypovascular cancer in hypoxia and uncernutrition state and the like, such as colon cancer.

Test Example 5

Three pancreas cancer patients who had been refractory to gemcitabine therapy carried out as pre-treatment were targeted and were daily administered orally with 3 g of the granule of Example 10 (containing 1 g of the burdock fruit extract powder) after breakfast once a day. In other words, 59.4 mg of arctigenin and 68.5 mg of arctiin were administered to the patients per day.

As a result, the tumors of these patients did not increase for 1 to 2 months after the beginning of the administering, however they were finally decided as PD. Therefore, neither tumor reducing effect nor lowering of the tumor markers was confirmed. In addition, no serious side effect after administration of the above granule was seen in any of the patients.

Example 12

Production of Burdock Fruit Extract by Cutting, Cold Extraction and Ethanol Addition The 200 g of chopped burdock fruit was added to 1 L of water (22° C.) and stirred for an hour, added by 0.45 L of ethanol and further heated to reflux for an hour. It was filtered by 4 sheets of gauze (100 mesh wire netting) and washed with 0.5 L of 30% ethanol, and the combined extraction solution (1.5 L) was freeze-dried. The burdock fruit extract which was obtained by cold extraction using cutting of herbal medicine contained 13.3% of arctigenin and 11.4% of arctiin respectively with arctigenin/arctiin (weight ratio)=0.86.

Test Example 6

Anticancerous Evaluation in Tumor Model Animal (Method for Test)

The model animal of a tumor was made by seeding human pancreas cancer cell line CAPAN-1 or PSN-1 in subcutis of back of a nude mouse (BALB-cAJnu/nu; CLEA Japan, Inc.) as a donor and transplanting the tumor mass of the provided donor mouse into subcutis of back of a recipient mouse, Arctigenin (AG), arctiin (A) and the burdock fruit extract (Example 12) were dissolved in DMSO in concentration of 10 mg/ml, diluted with a saline, and then administered orally in stomach at 50 μg per one mouse five times a week. The anticancerous was evaluated by measuring the size of the subcutaneous tumor mass of the back with time.

Figure 4:
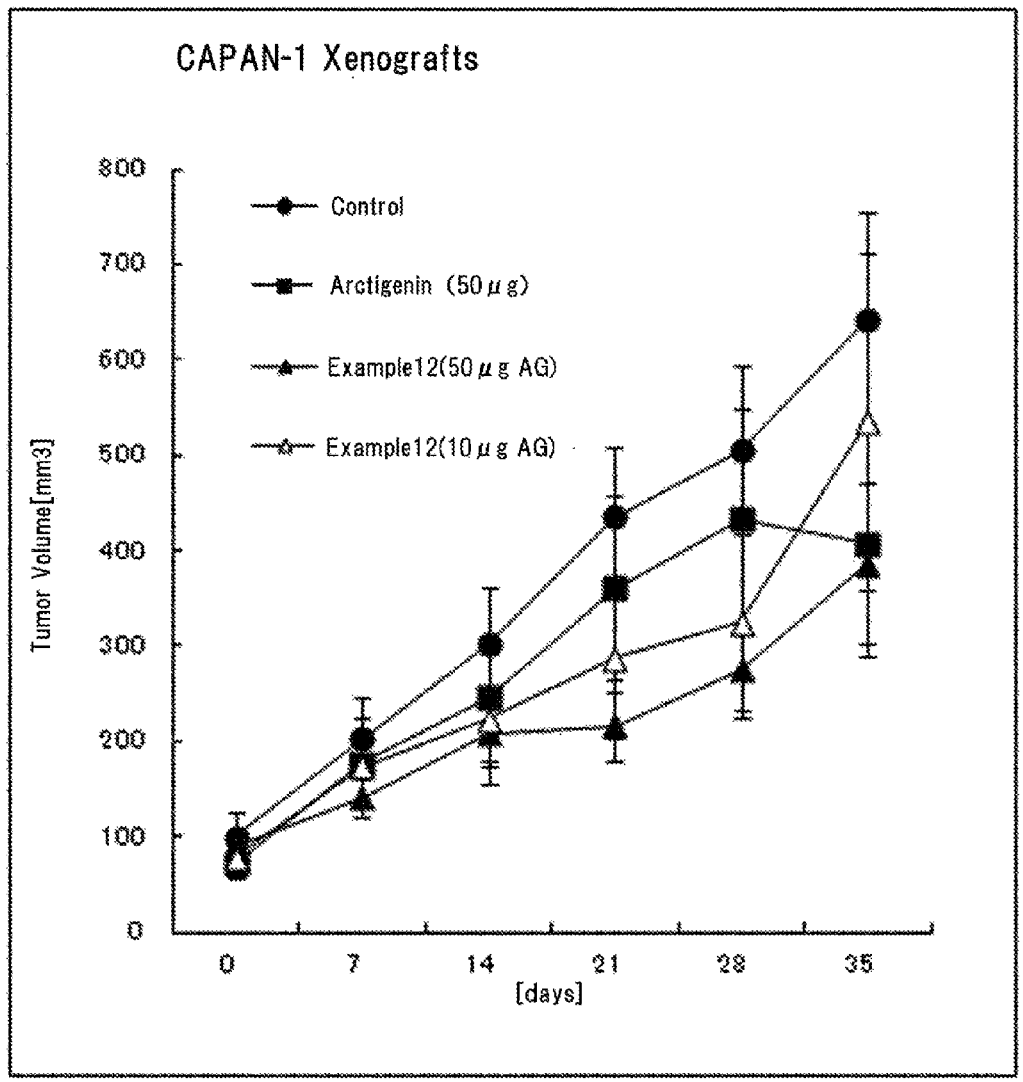
FIG. 4 shows the results of the antitumor evaluation in the model animal of the tumor (CAPAN-1 Xenografts).
Figure 5:
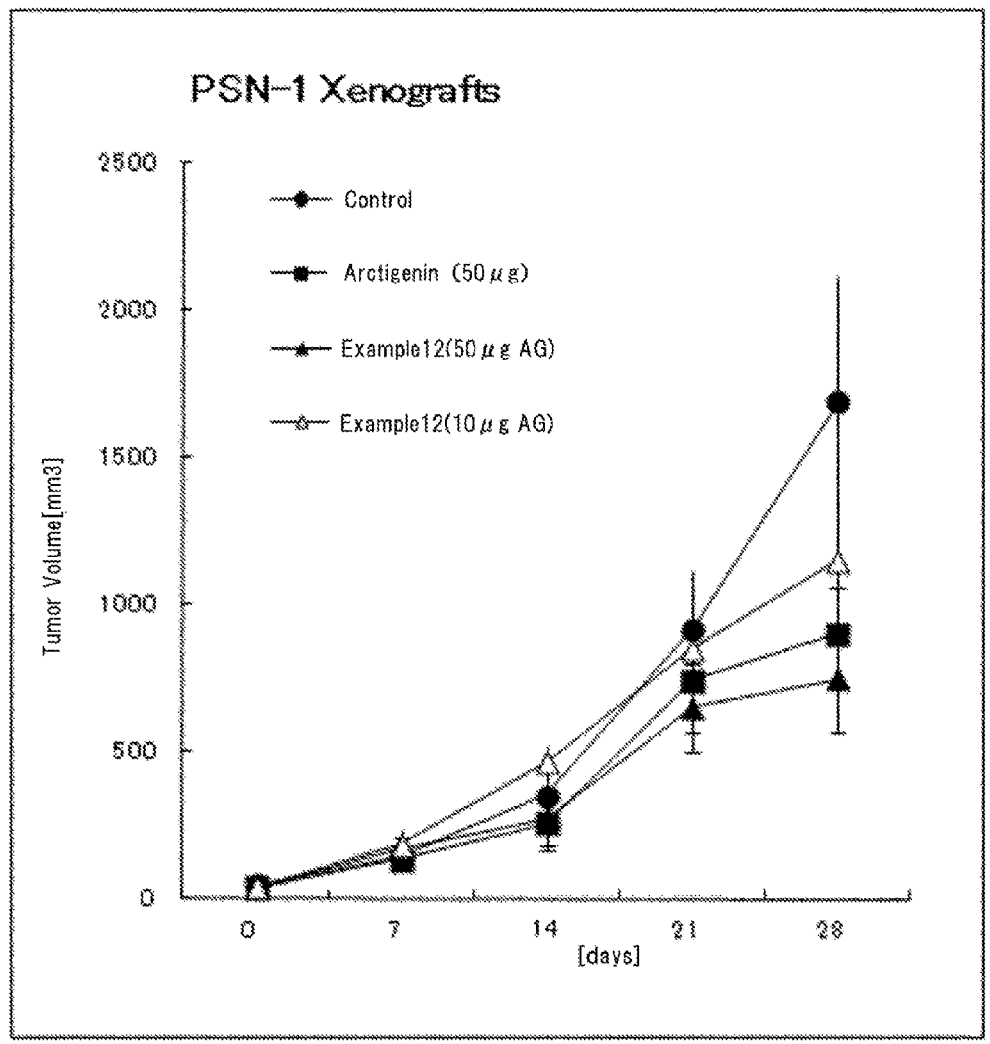
FIG. 5 shows the results of the antitumor evaluation in the model animal of the tumor (PSN-1 Xenografts).

The remarkable inhibiting effect on tumor growth was seen in the agent administered group compared with control in one month after the beginning of the administering. The antitumor effect was also obtained in the group administered with purified arctigenin, however, the stronger antitumor effect was seen in the burdock fruit extract (Example 12) containing the precursor arctiin together (FIGS. 4 and 5). It was confirmed that the burdock fruit extract with arctigenin/ arctiin (weight ratio)=0.7 to 1.3 showed higher antitumor activity.

Test Example 7

Expression Frequency of Dose Limiting Toxicity (DLT)

By targeting the 15 pancreas cancer patients who had been refractory to gemcitabine therapy carried out as pre-treatment, the phase I study of the granule containing arctigenin was carried out to investigate the expression frequency of dose limiting toxicity. These 15 patients were daily administered orally with predetermined dose of the granule containing arctigenin after breakfast once a day. Three of these 15 patients were administered with 3 g of the granule of Example 10 (containing 1 g of the burdock fruit extract powder, namely 59.4 mg of arctigenin and 68.5 mg of arctiin) per once. Another three of these 15 patients were administered with 7.5 g of the granule of Example 10 (containing 2.5 g of the burdock fruit extract powder namely 148.5 mg of arctigenin and 171.25 mg of arctiin) per once. Still another nine patients were administered with 12 g of the granule of Example 10 (containing 4 g of the burdock fruit extract powder namely 237.6 mg of arctigenin and 274 mg of arctiin) per once.

As a result, among these 15 targeted patients, the expression frequency of dose limiting toxicity was 0. Specifically, the main adverse events of Grade 3 or more in the phase I study of the granule containing arctigenin against the pancreas cancer patient were a rise of GGT, hyperglycemia, a rise of the ALP and a rise of blood bilirubin, and therefore no serious adverse event was observed.

TABLE 4

Adverse event in the phase I study of the granule containing arctigenin (n = 15, during all course periods)

| Item | G1 | G2 | G3 | G4 | % G 3-4 |
|---|---|---|---|---|---|
| Subjective and objective symptom | | | | | |
| Diarrhea | 3 | 1 | 0 | 0 | 0 |
| Nausea | 2 | 2 | 0 | — | 0 |
| Stomachache | 1 | 0 | 0 | — | 0 |
| Vomiting | 3 | 0 | 0 | 0 | 0 |
| Inappetence | 3 | 4 | 0 | 0 | 0 |
| Laboratory values | | | | | |
| Leukopenia | 5 | 0 | 0 | 0 | 0 |
| Neutropenia | 1 | 0 | 0 | 0 | 0 |
| Anemia | 11 | 2 | 0 | 0 | 0 |
| Thrombocytopia | 3 | 0 | 0 | 0 | 0 |
| Blood bilirubin increase | 1 | 1 | 1 | 0 | 6.67 |
| AST increase | 9 | 2 | 0 | 0 | 0 |
| ALT increase | 6 | 1 | 0 | 0 | 0 |
| ALP increase | 10 | 1 | 1 | 0 | 6.67 |
| GGT increase | 4 | 0 | 7 | 0 | 46.7 |
| Cr increase | 0 | 1 | 0 | 0 | 0 |
| Hyperglycemia | 5 | 6 | 4 | 0 | 26.7 |

It was found from these result that the granule of the Examples had very low toxicity and high safety. Therefore, it has been shown that the present invention can provide an anticancer agent with fewer side effects.

Test Example 8

Effect on Pancreas Cancer Stem Cell

Then, the effect of arctigenin on cancer stem-like cells (CSCs), which was considered to be deeply involved in various treatment resistance, recurrences and appearance of metastases in cancer, was examined.

(Preparation of Medium and Reagent)

For preparation of the glucose-containing medium, 4.75 g of Dulbecco's modified Eagle medium 2 (Nissui Pharmaceutical) was dissolved in water, added by 12.5 ml of 1M HEPES pH 7.4 (DOJINDO LABORATORIES, 342-01375), sterilized, added by 18.5 ml of 10% NAHCO$_3$, 10 ml of L-glutamine (Sigma-Aldrich), 5 ml of Anti-Anti (Life technologies), 5 ml of MEM NON-ESSENTIAL AMINO ACID SOLUTION (Sigma-Aldrich) and 50 ml of FETAL BOVINE SERUM (Biowest) that was inactivated in a warm bath at 56° C. for 30 minutes, and finally filled up to 500 ml.

The glucose inhibition medium was prepared by adding 2-Deoxy-Glucose (2-DG) (Tokyo Chemical Industry) in 20 mM of final concentration to the glucose-containing medium.

The medium containing 3 µM arctigenin was prepared by adding arctigenin (Kracie Pharmaceutical) in 3 µM of final concentration to the glucose-containing medium or the glucose inhibition medium.

For preparation of FACS buffer, 10 g of Bovine serum albumin Protease free (Wako Pure Chemical industries) was dissolved in 1 L of PBS (−), added by sodium azide in 0.1% of final concentration and performed filtration sterilization.

For the fluorescence-labeled antibody for FACS assays, CD44 (338803 or 338807, BioLegend), CD24 (311117, BioLegend), ESA (324205, BioLegend) and c-Met (11-8858, eBioscience) were used. In addition, a staining step was carried out according to the attached data sheet to the product.

(Method for Test and Results)

The pancreas cancer cell PANC-1 (ATCC No CRL-1469 was seeded in a glucose-containing medium, incubated overnight and then incubated in each of the glucose-containing medium, the glucose inhibition medium, the glucose-containing medium containing 3 µM arctigenin and the glucose inhibition medium containing 3 µM arctigenin for 24 hours. After collected cells, PI staining (dead cell staining) and cancer stem cell marker staining were carried out according to the usual method and an Analysis was carried out using flow cytometry (FACS). For a marker, triple positive of CD44, CD24 and ESA (CD326) or double positive of CD44 positive and c-Met strong positive which were reported as a stem cell marker of pancreas cancer were used.

Figure 6:
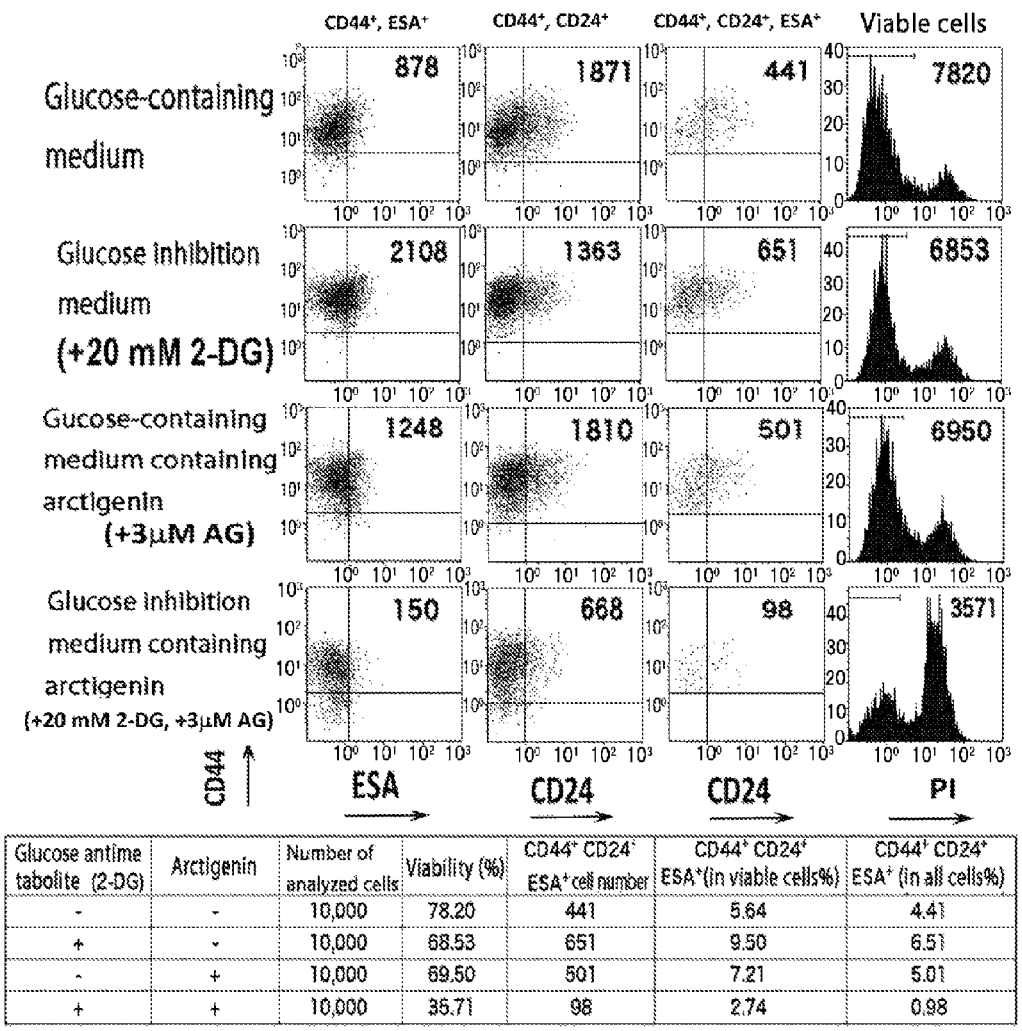
FIG. 6 shows the results of the PI staining and the pancreas cancer stem cell marker (CD44, CD24 and ESA) staining for cancer stem cell.

FIG. 6 shows the results of P1 staining and cancer stem cell marker (triple positive of $CD44^+$, $CD24^+$ and $ESA^+$ (CD326)) staining. As a result of PI staining, the cellular survival rate was 78.20% for the glucose-containing condition, 68.53% for the glucose inhibition condition and 69.50% for the glucose-containing condition in the presence of 3 µM arctigenin, whereas the survival rate was 35.71% for the glucose inhibition condition in the presence of 3 µM arctigenin.

In addition, as a result of the cancer stem cell marker staining, the ratio (the number of the survival) of $CD44^+$ $ESA^+CD24^+$ cell which indicated a pancreas cancer stem cell was 4.41% (441) for the glucose-containing condition, 6.51% (651) for the glucose inhibition condition and 5.01% (501) for the glucose-containing condition in the presence of 3 µM arctigenin, whereas 0.98% (98) for the glucose inhibition condition in the presence of 3 µM arctigenin in all analyzed cells. Therefore, it was shown that arctigenin has an effect of killing pancreas cancer stein cell under the glucose starvation condition.

Figure 7:
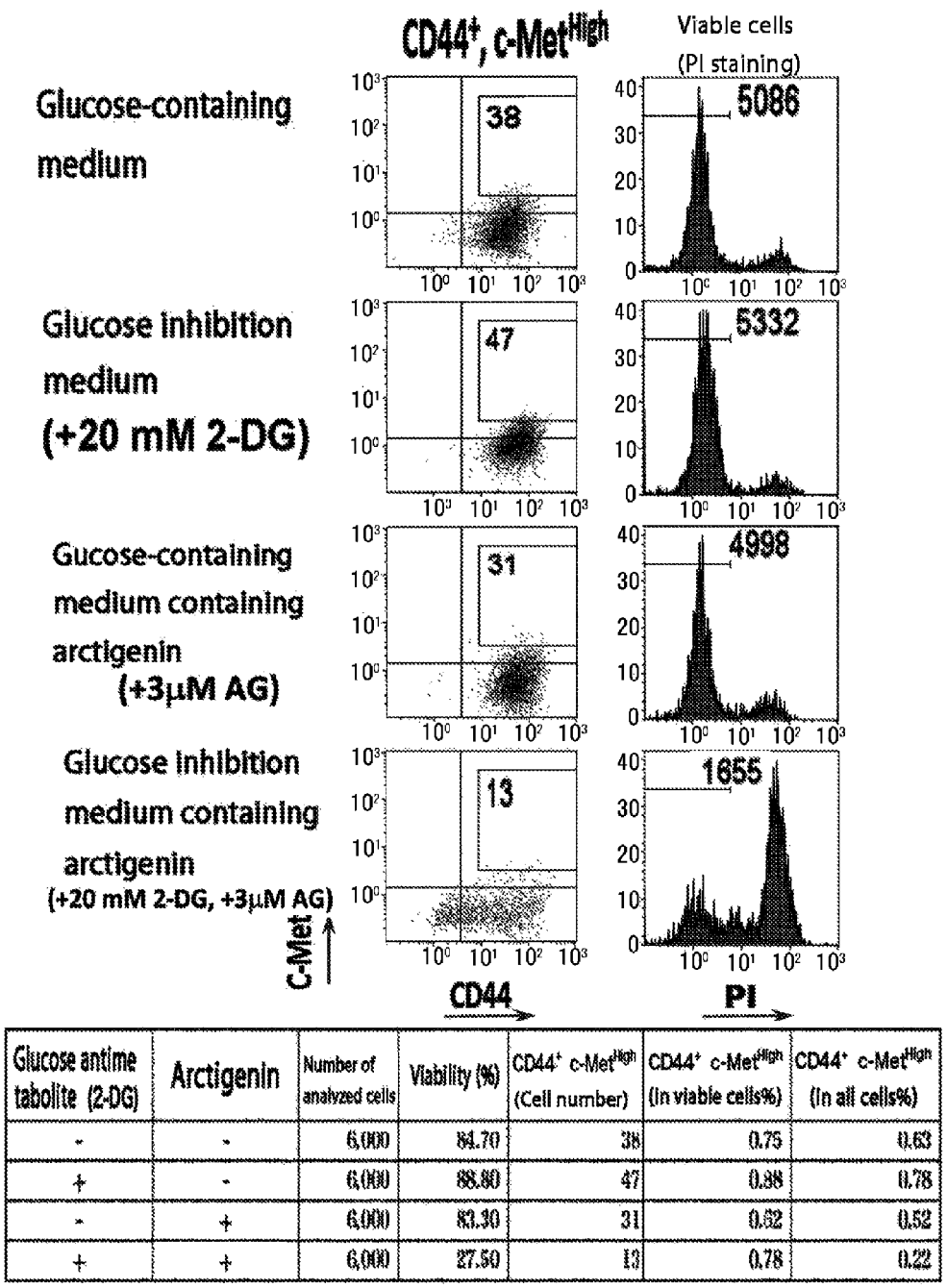
FIG. 7 shows the results of the PI staining and the pancreas cancer stem cell marker (CD44 and c-Met) staining for cancer stem cell.

FIG. 7 shows the results of PI staining and cancer stem cell marker (double positive of $CD44^+$ and $c\text{-}Met^{High}$) staining. As a result of PI staining, the cellular survival rate was 84.70% under the glucose-containing condition, 88.80% under the glucose inhibition condition and 83.30% under the presence of 3 µM arctigenin in the glucose-containing condition, whereas the survival rate was 27.50% under the presence of 3 µM arctigenin in the glucose inhibition condition.

The positive ratio (the number of the survival) of CD44 positive c-Met strong positive ($CD44^+$,$c\text{-}Met^{High}$) cell, which was reported one after another as a new marker of pancreas cancer stem cell using a strong tumorigenicity as an indicator was 0.63% (38) for the glucose-containing condition, 0.78% (47) for the glucose inhibition condition and 0.52% (31) for the glucose-containing condition in the presence of 3 µM arctigenin, whereas 0.22% (13) for the glucose inhibition condition in the presence of 3 µM arctigenin in all analyzed cells. Therefore, it has been shown that arctigenin has an effect of killing pancreas cancer stem cell under a glucose starvation condition. Therefore, it has been shown that arctigenin also has an effect of killing pancreas cancer stem cell that expresses these stern cell markers under the glucose starvation condition.

Test Example 9

Comparative Test with Preexisting Chemotherapeutic Agent Against Pancreas Cancer Stem Cell The effect of killing pancreas cancer stem cell of arctigenin was compared with that of cisplatin which was one of the preexisting chemotherapeutic agents against pancreas cancer.

(Preparation of Medium and Reagent)

For preparation of the glucose-containing medium, 4.75 g of Dulbecco's modified Eagle medium 2 (Nissui Pharmaceutical) was dissolved in water, added by 12.5 ml of 1M HEPES pH 7.4 (DOJINDO LABORATORIES, 342-01375), sterilized, added by 18.5 ml of 10% $NAHCO_3$, 10 ml of L-glutamine (Sigma-Aldrich), 5 ml of Anti-Anti (Life technologies), 5 ml of MEM NON-ESSENTIAL AMINO ACID SOLUTION (Sigma-Aldrich) and 50 ml of FETAL BOVINE SERUM (Biowest) that was inactivated in a warm bath at 56° C. for 30 minutes, and finally filled up to 500 ml.

The glucose inhibition medium was prepared by adding 2-Deoxy-Glucose (2-DG) (Tokyo Chemical industry) in 15 mM of final concentration to the glucose-containing medium.

The medium containing 4 µM arctigenin was prepared by adding arctigenin (Kracie Pharmaceutical) in 4 µM of final concentration to the glucose-containing medium or the glucose inhibition medium.

(Method for Test and Results)

The pancreas cancer cell Capan-1 (ATCC No. HTB-79) was seeded in a glucose-containing medium, incubated overnight and then incubated in each of a glucose-containing medium, a glucose inhibition medium, a glucose-containing medium containing 4 µM arctigenin and a glucose inhibition medium containing 4 µM arctigenin, or in 7 µM cisplatin (CDDP: Wako Pure Chemical Industries) for 24 hours. After collected cells, PI staining (dead cell staining) and cancer stem cell marker staining were carried out according to the usual method and an Analysis was carried out using flow cytometry (FACS). For the marker, triple positive of CD44, CD24 and ESA (CD326) which was reported as a stern cell marker of pancreas cancer was used.

Figure 8:
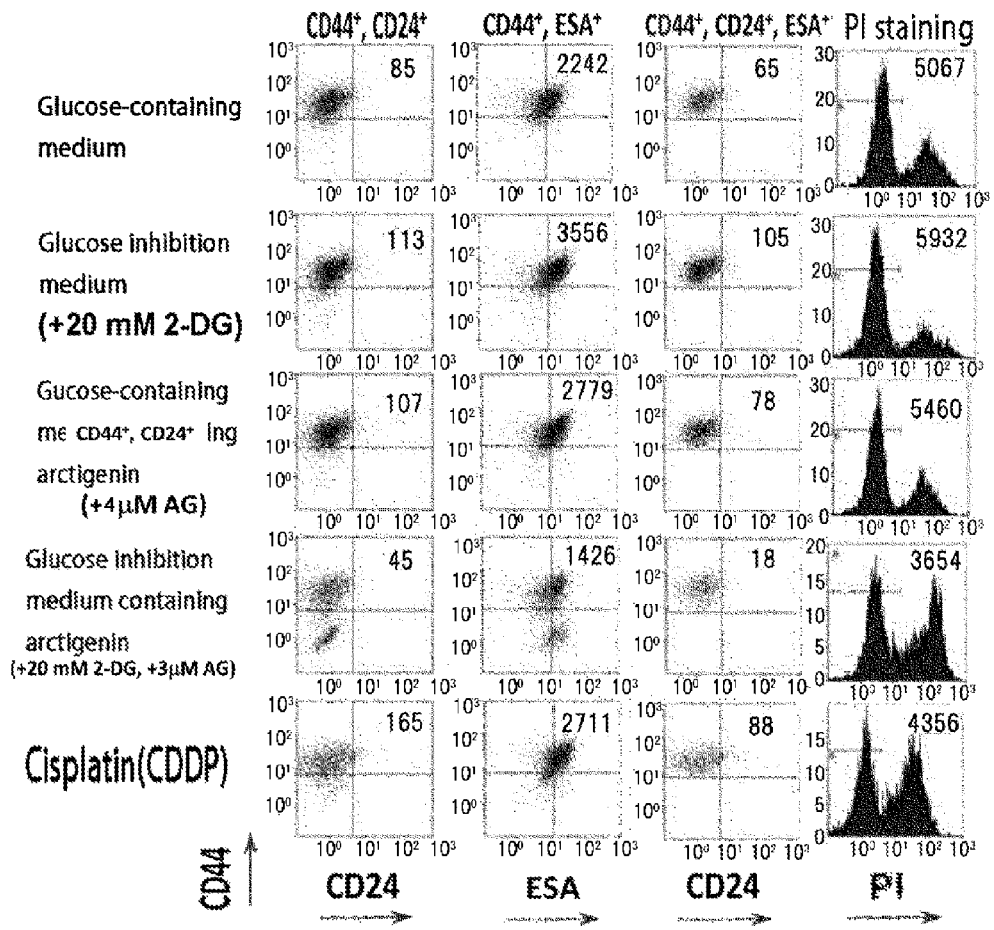
FIG. 8 shows the results of the PI staining and the pancreas cancer stem cell marker staining for cancer stem cell (comparison with the cisplatin treating).

FIG. 8 shows the results of PI staining and cancer stem cell marker staining. As a result of PI staining, the cellular survival rate was 67.57% for the glucose-containing condition, 79.10% for the glucose inhibition condition and 72.80% for the glucose-containing condition in the presence of 4 µM arctigenin, whereas the survival rate was 48.73% for the glucose inhibition condition in the presence of 4 µM arctigenin and 58.08% under the cisplatin treatment.

In addition, as a result of the cancer stem cell marker staining, the ratio (the number of the survival) of $CD44^+$ $ESA^+CD24^+$ cell which is indicative of the pancreas cancer stem cell was 0.87% (65) for the glucose-containing condition, 1.40% (105) for the glucose inhibition condition and 1.04% (78) for the glucose-containing condition in the presence of 4 μM arctigenin, whereas 0.24% (18) for the glucose inhibition condition in the presence of 4 μM arctigenin and 1.17% (88) for the cisplatin treatment in all analyzed cells. On the other hand, when they were analyzed in viable cells, 1.28% for the glucose-containing condition, 1.77% for the glucose inhibition condition and 1.43% for the glucose-containing condition in the presence of 4 μM arctigenin, whereas 0.50% for the glucose inhibition condition in the presence of 4 μM arctigenin, and it rose to 2.02% for the cisplatin treatment. Therefore, it has been shown that arctigenin has an effect for killing $CD44^+ESA^+CD24^+$ positive pancreas cancer stem cell which is difficult to be killed by cisplatin under the glucose starvation condition.

It has been strongly suggested from the results of the test examples 8 and 9 that arctigenin has the effect of killing cancer stem-like cells in the nutrition starvation condition which is close to the environment where cancer cell is placed in the body. In addition, it has been strongly suggested that arctigenin has not only the effect of inhibiting the growth of cancer cell by acting on tumor body but also the effect of acting on and killing cancer stem cell which can supply cancer cell and reconstruct tumor tissue.

In addition, the granule containing arctigenin in the test example 7 showed very low toxicity. Arctigenin has the killing effect in the nutrition starvation condition and acts on not only cancer body cell but also cancer stem cell, so that it is suggested that arctigenin can lower the influence on normal cell and may acquire the low toxicity. Therefore, the present invention can provide an anticancer agent having high anticancer activity with few side effects.

INDUSTRIAL APPLICABILITY

The present invention can be preferably used for an anticancer agent especially a pancreas cancer therapeutic agent.

What is claimed is:
1. A method of treating pancreatic cancer comprising administering to a human patient in need thereof, a dose of arctigenin of at least 148.5 mg per day.
2. The method of claim 1, further comprising administering to said patient a dose of arctiin of at least 171.25 mg per day.
3. The method of claim 1 or claim 2, wherein said pancreatic cancer is refractory to treatment with gemcitabine.
4. The method of claim 2, wherein said method of treating pancreatic cancer comprises reducing recurrences and metastases of pancreatic cancer which occur after cancer treatment.
5. A method of inhibiting pancreatic cancer stem cells comprising administering to said human patient in need thereof, a composition comprising arctigenin at a dose of at least 148.5 mg or more per day.
6. A method for reducing recurrences and metastases of pancreatic cancer which occur after cancer treatment in a human patient, comprising administering a composition containing arctigenin in a dose of at least 148.5 mg per day to said patient.

* * * * *